(12) United States Patent
Chen

(10) Patent No.: US 11,181,755 B2
(45) Date of Patent: Nov. 23, 2021

(54) EYEGLASSES ASSEMBLING STRUCTURE HAVING ANCILLARY FRAME

(71) Applicant: PROHERO GROUP CO., LTD., Tainan (TW)

(72) Inventor: Pen-Wei Chen, Tainan (TW)

(73) Assignee: Prohero Group Co., Ltd., Tainan (TW)

(*) Notice: Subject to any disclaimer, the term of this patent is extended or adjusted under 35 U.S.C. 154(b) by 272 days.

(21) Appl. No.: 16/553,600

(22) Filed: Aug. 28, 2019

(65) Prior Publication Data
US 2021/0063772 A1    Mar. 4, 2021

(51) Int. Cl.
*G02C 9/04* (2006.01)
*A61F 9/02* (2006.01)

(52) U.S. Cl.
CPC . *G02C 9/04* (2013.01); *A61F 9/02* (2013.01)

(58) Field of Classification Search
CPC . G02C 9/04; G02C 5/124; G02C 9/02; G02C 2200/18; A61F 9/02; A61F 9/029
See application file for complete search history.

(56) References Cited

U.S. PATENT DOCUMENTS

| | | | | |
|---|---|---|---|---|
| 5,170,502 A | * | 12/1992 | Hegendorfer | G02C 5/12 2/13 |
| 5,412,438 A | * | 5/1995 | Bolle' | G02C 5/126 351/138 |
| 5,790,230 A | * | 8/1998 | Sved | A61F 9/025 351/110 |
| 5,929,963 A | * | 7/1999 | McNeal | G02C 9/00 351/47 |
| 6,502,937 B2 | * | 1/2003 | Yang | G02C 1/00 351/47 |
| 2011/0083256 A1 | * | 4/2011 | Wang-Lee | G02C 9/04 2/434 |

* cited by examiner

*Primary Examiner* — Tuyen Tra
(74) *Attorney, Agent, or Firm* — Rosenberg, Klein & Lee

(57) ABSTRACT

An eyeglasses assembling structure having an ancillary frame is disclosed herein. It mainly comprises a main frame, an ancillary frame, a connecting part correspondingly engaged with the main frame at a lower end thereof and having plural engaging slots at an upper end thereof, an adjusting element having plural protrusions and an orientation part, and an engaging part disposed on the ancillary frame and correspondingly engaged with the adjusting element to adjust a rotation angle of the ancillary frame, wherein each of the plural protrusions engages with one of the plural engaging slots to adjust distance from the connecting part to the ancillary frame.

10 Claims, 8 Drawing Sheets

EYEGLASSES ASSEMBLING STRUCTURE HAVING ANCILLARY FRAME

BACKGROUND OF THE INVENTION

1. Field of the Invention

This invention relates to an eyeglasses assembling structure having an ancillary frame which comprises an adjustable ancillary frame disposed at an inner side of a main frame for adjusting an appropriate height, distance and angle of the ancillary frame on the main frame according to the needs of different wearers.

2. Description of Related Art

With the development of the social economy and the implementation of the two-day weekend, people began to pay attention to leisure activities. The outdoor leisure style that advocates nature is prevalent, and it also brings the craze for sightseeing and promotes people's willingness to travel or go out, e.g. surfing in the tropics, snorkeling, skiing in the cold regions, visiting interesting places and the like.

In general, users can only choose vision correction optical lenses, sunglasses, goggles or snow mirrors to wear. Although users wearing myopia glasses have clear vision, but they cannot wear sunglasses, wind goggles or snow goggles at the same time to avoid the damage by ultraviolet rays caused by excessive sunlight.

The conventional sunglasses, wind goggles, snow goggles and industrial goggles typically do not provide function of vision correction. Therefore, eyeglasses having a main frame and a secondary frame have been developed. Specifically, the main frame is equipped with vision correction optical lenses, and the secondary frame is provided with lenses for protection against ultraviolet rays, snow, dust or flying debris. Furthermore, the main frame and the secondary frame are combined with each other by magnets and the like. With this eyeglass design, users can save on the cost of making sunglasses, wind goggles, snow goggles or industrial goggles for vision correction and protection against ultraviolet rays, snow, sand or flying debris. However, the above eyeglasses is not cheap enough, and the main frame and the secondary frame are easily loose after a period of use. Additionally, the main frame and the secondary frame occupy a large space.

In order to shield light or isolate dust or flying debris from multiple angles and directions, wind goggles, snow goggles or industrial goggles are usually equipped with large glasses. Therefore, protective lenses can be adopted in the main frame, and optical lenses with vision correction function can be adopted in the secondary frame so as to completely cover the user's eyes and around the eyes and achieve a double effect. Although the above eyeglasses achieves the double effect, the main frame and the secondary frame cannot be adjusted according to the needs of different wearers. Therefore, when the different wearers actually wear the above structure, due to the difference in face shapes, nose heights and diopters, there is a discrepancy in viewing distance.

SUMMARY OF THE INVENTION

The present invention is aimed to provide an eyeglasses assembling structure having an ancillary frame which comprises an adjustable ancillary frame disposed at an inner side of a main frame for adjusting an appropriate height, distance and angle of the ancillary frame on the main frame according to the needs of different wearers.

The eyeglasses assembling structure having an ancillary frame of this invention is achieved by the following technical features. It comprises a main frame, an ancillary frame, a connecting part, an adjusting element and an engaging part. The connecting part is correspondingly engaged with the main frame at a lower end thereof and further provided with a plurality of engaging slots at an upper end thereof. The adjusting element is provided with a plurality of protrusions and an orientation part, and each of the plural protrusions engages with one of the plural engaging slots to adjust distance from the connecting part to the ancillary frame. The engaging part is disposed on the ancillary frame and correspondingly engaged with the adjusting element to adjust a rotation angle of the ancillary frame.

Accordingly, the ancillary frame can be correspondingly assembled in the main frame, and the height, the distance and the angle of the ancillary frame on the main frame can be adjusted according to the needs of different wearers so as to achieve effects of improving the clarity of viewing and the comfort of wearing.

DETAILED DESCRIPTION OF THE PREFERRED EMBODIMENT

In the following detailed description, for purposes of explanation, numerous specific details are set forth in order to provide a thorough understanding of the disclosed embodiments.

Figure 1:
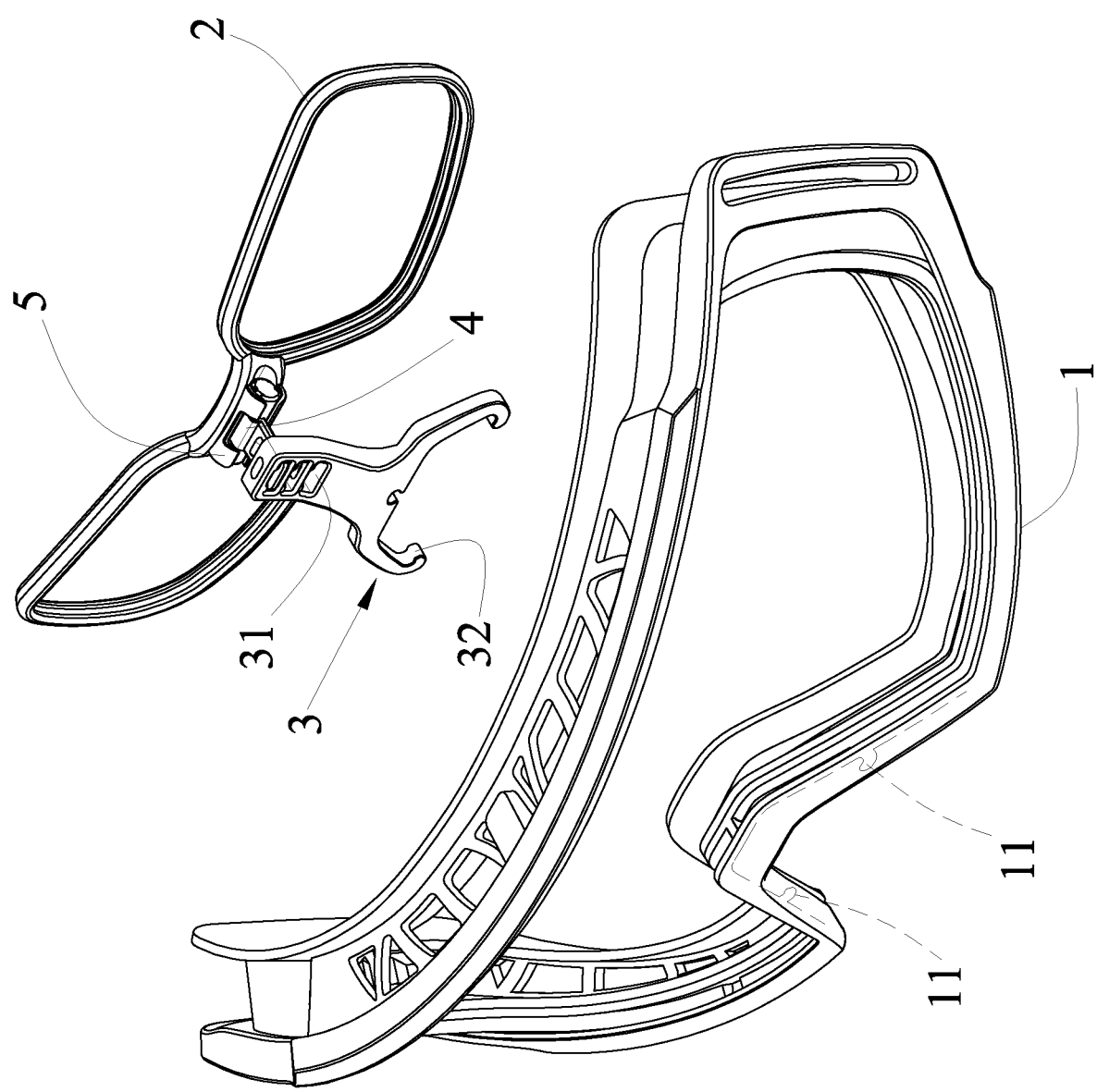
FIG. 1 is an explosion diagram showing an eyeglasses assembling structure having an ancillary frame according to the present invention.
Figure 2:
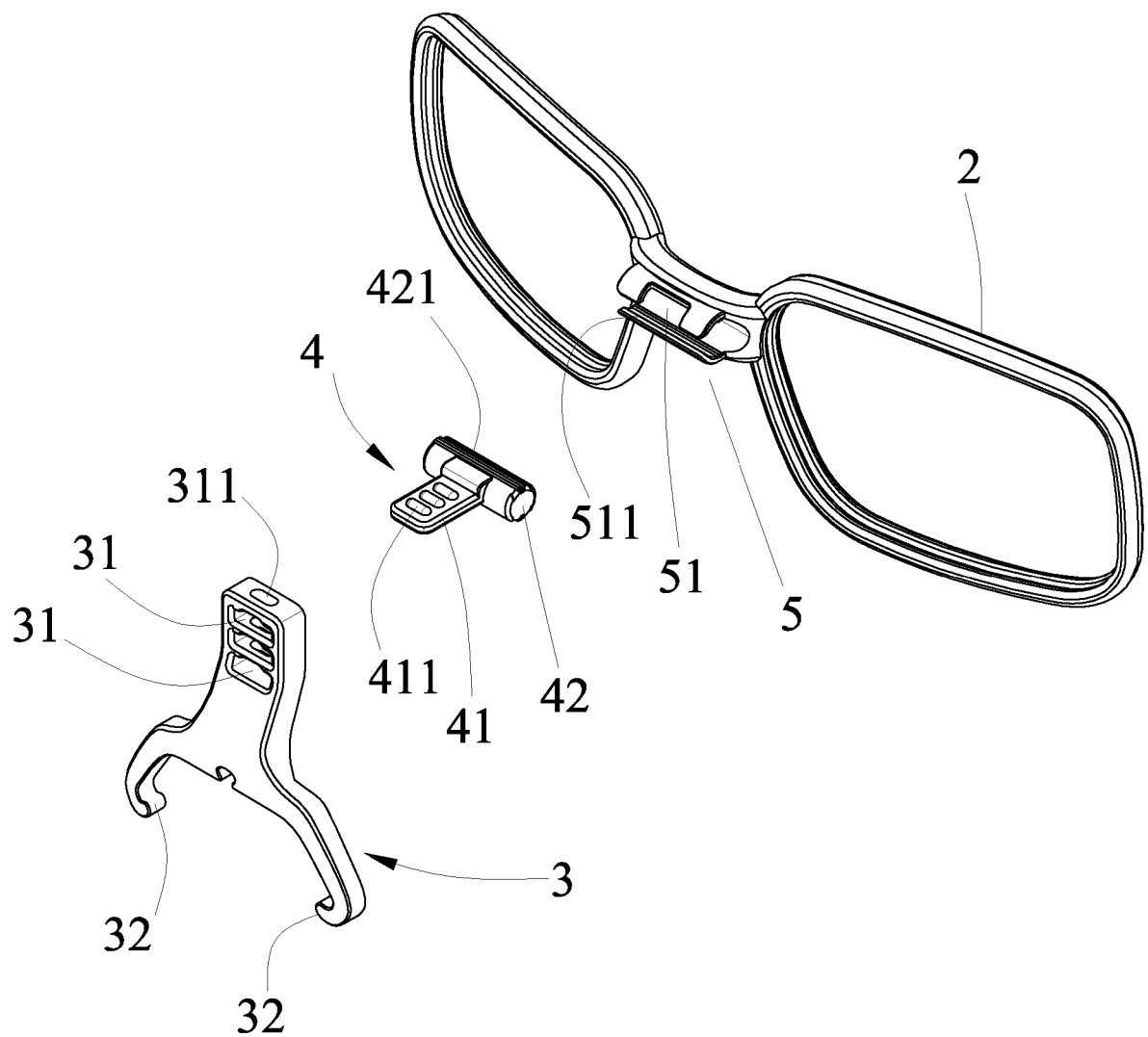
FIG. 2 is a partial explosion diagram of the present invention.
Figure 3:
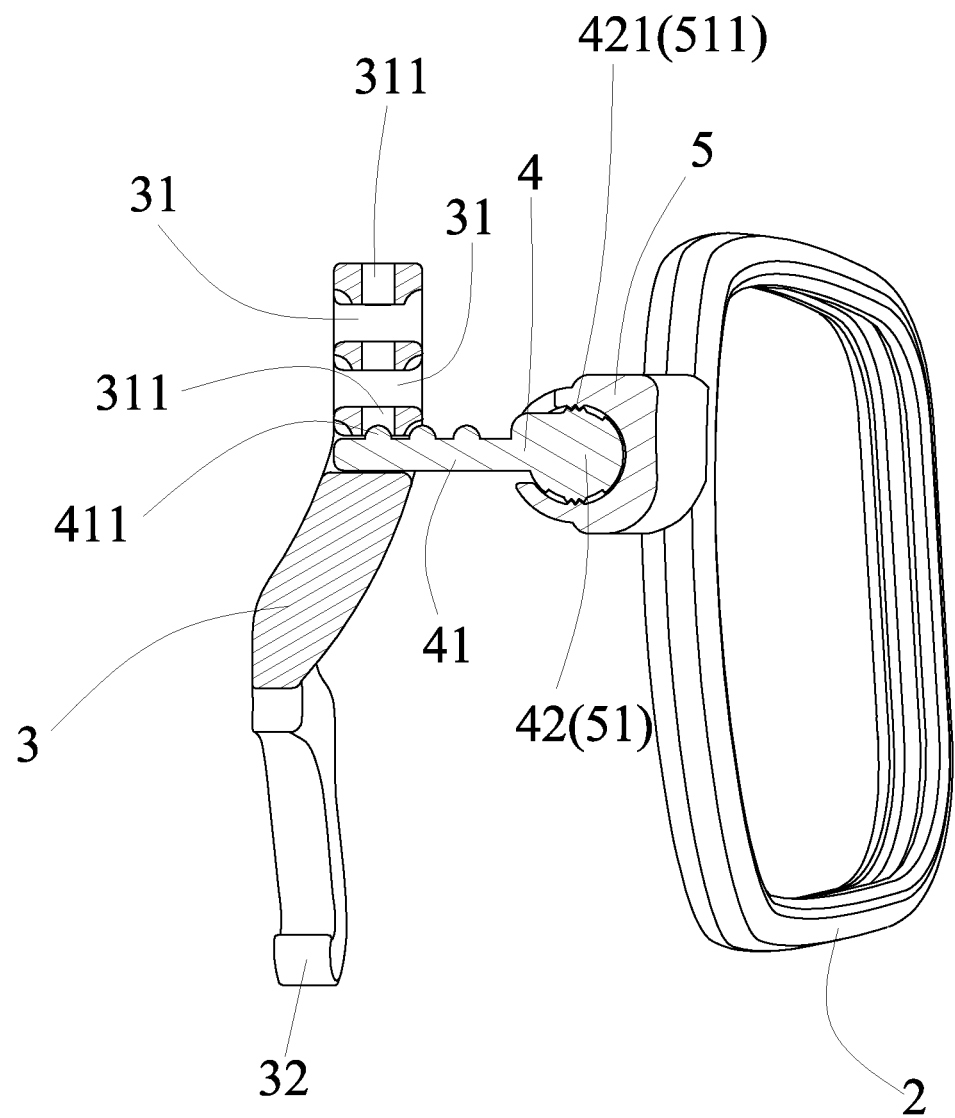
FIG. 3 is a schematic diagram showing an inserting sheet is inserted into one of a plurality of engaging slots to adjust a height according to the present invention.
Figure 4:
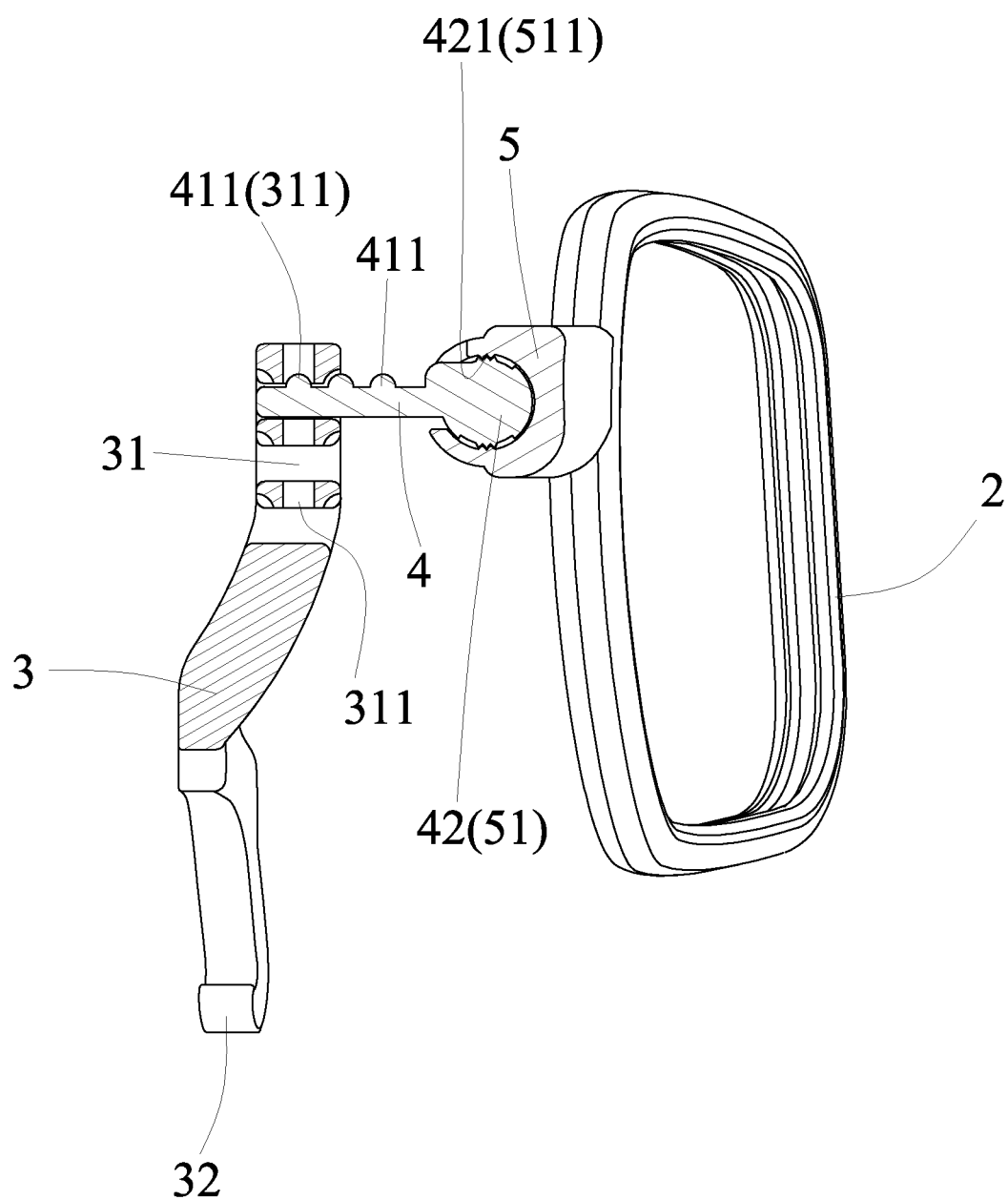
FIG. 4 is a schematic diagram showing a height of an ancillary frame on a connecting part and a distance from the connecting part to the ancillary frame are respectively adjusted by an inserting sheet and a plurality of protrusions on the inserting sheet of an adjusting element according to the present invention.
Figure 5:
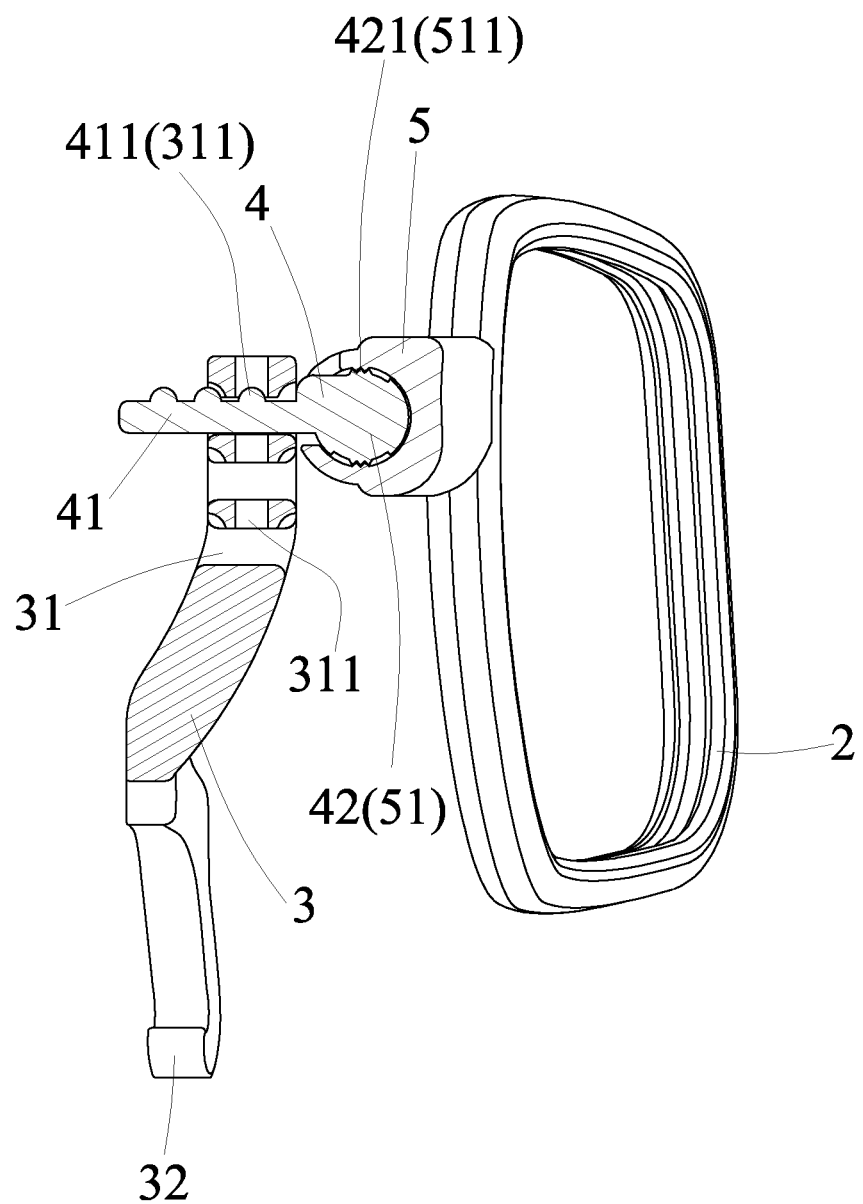
FIG. 5 is a schematic diagram showing a distance from a connecting part to an ancillary frame is adjusted by an adjusting element according to the present invention.
Figure 6:
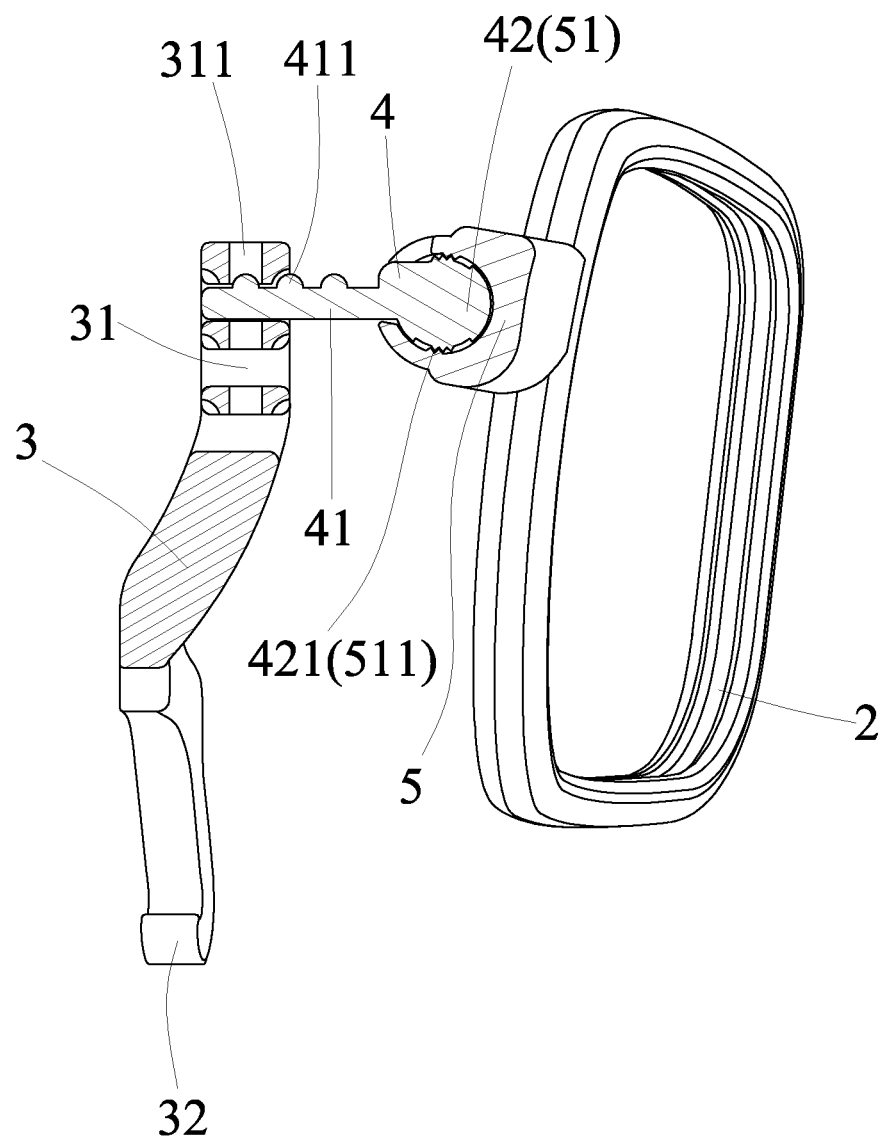
FIG. 6 is a first schematic diagram showing an ancillary frame is rotated at an angle by an engaging part according to the present invention.
Figure 7:
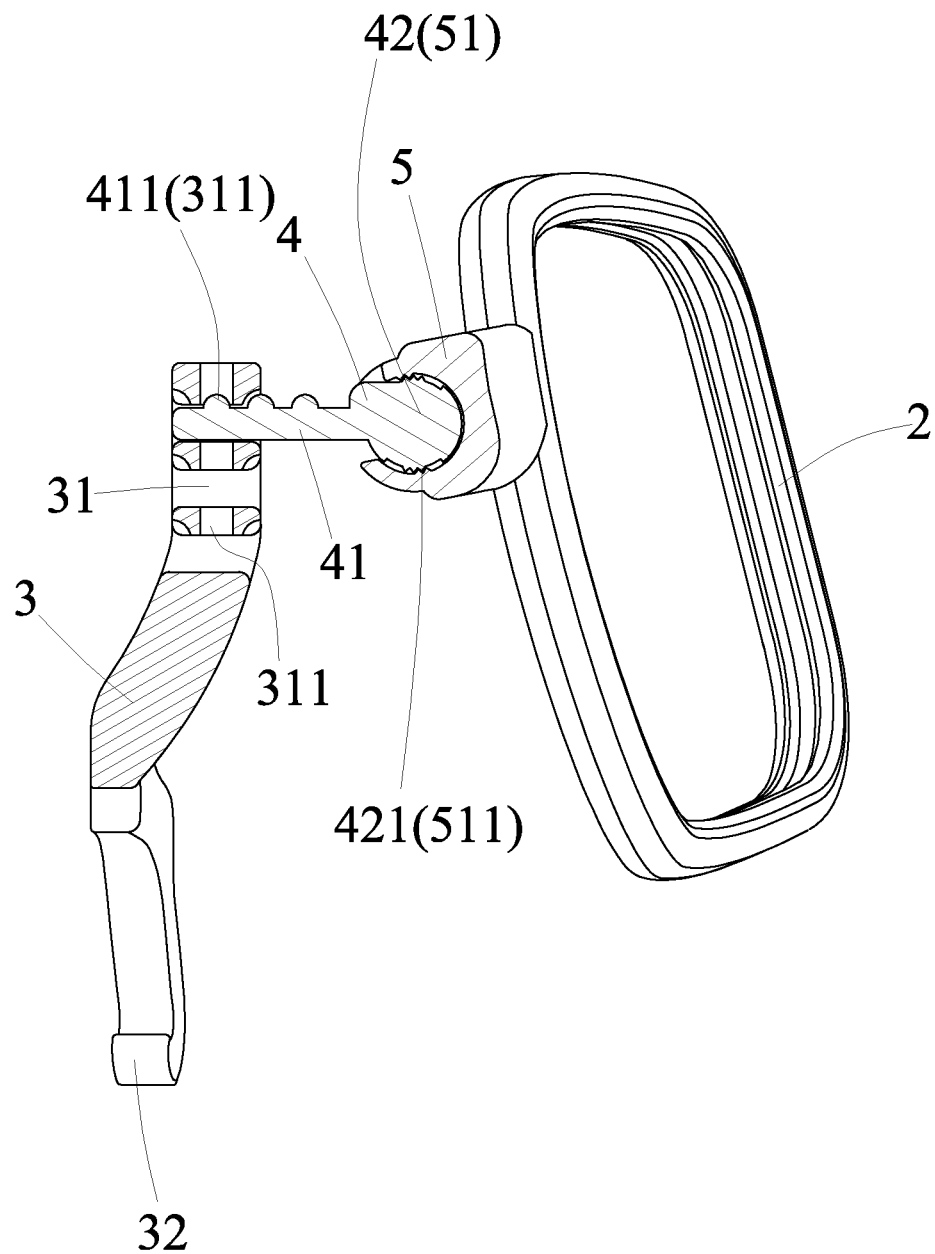
FIG. 7 is a second schematic diagram showing an ancillary frame is rotated at an angle by an engaging part according to the present invention.

Referring to FIG. 1, FIG. 2 and FIG. 3, an eyeglasses assembling structure having an ancillary frame is disclosed herein. It mainly comprises a main frame (1), an ancillary frame (2), a connecting part (3), an adjusting element (4) and an engaging part (5). The connecting part (3) is assembled to the main frame (1) at a lower end thereof and having a plurality of engaging slots (31) at an upper end thereof. The adjusting element (4) is provided with an inserting sheet (41)

at a first end thereof and an orientation part (42) at a second end thereof, and the inserting sheet (41) is engaged with one of the plurality of engaging slots (31) for positioning. The engaging part (5) is disposed on the ancillary frame (2) and provided with a receiving slot (51) for engaging with the orientation part (42) of the adjusting element (4) to adjust angles and positions.

Referring to FIG. 1 to FIG. 7, the invention can be applied to different additional frames. For instance, the main frame (1) is a wind goggle, a snow goggle or an industrial goggle. The ancillary frame (2) is optical glasses, e.g. myopia glasses, hyperopia glasses or vision correction glasses.

Figure 8:
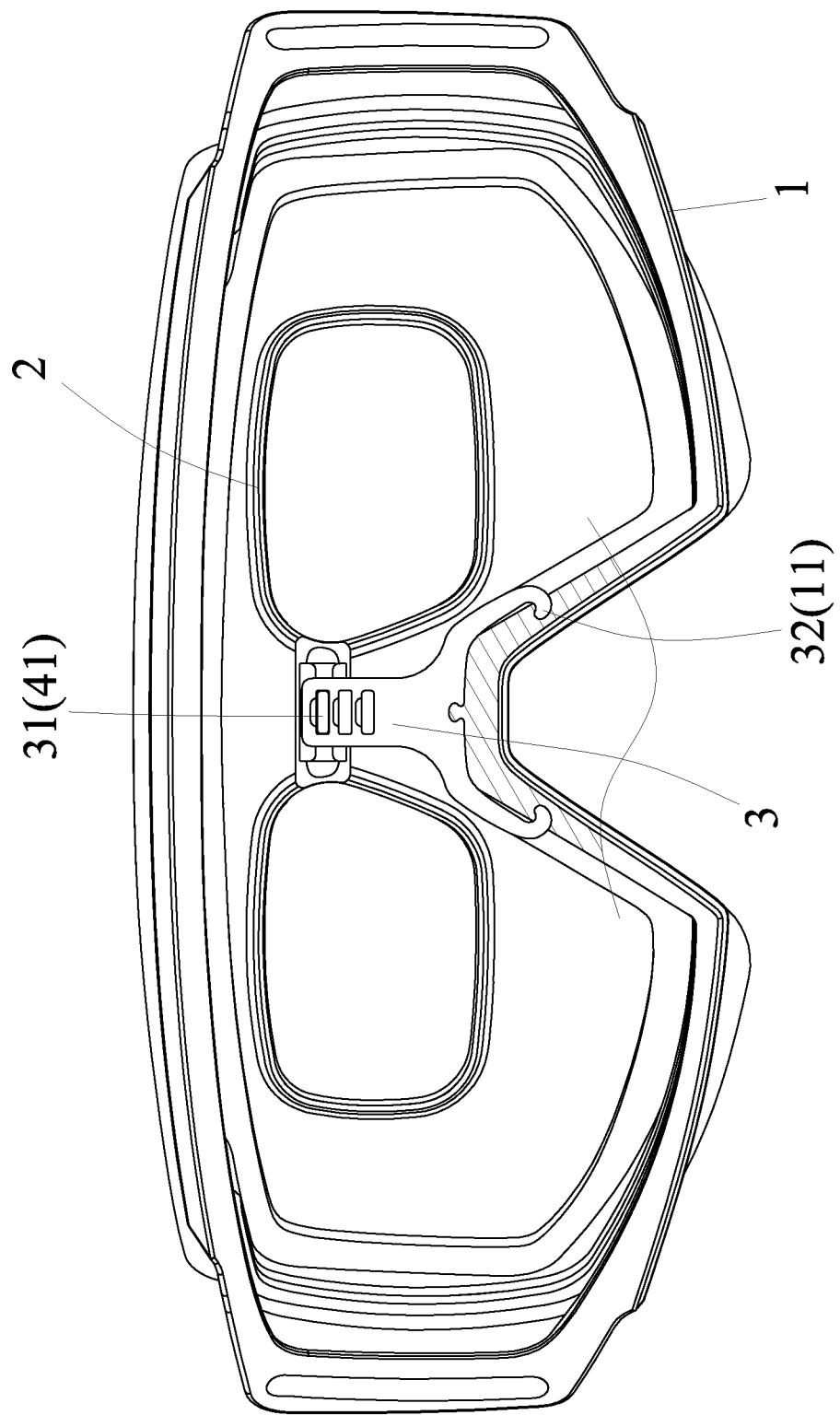
FIG. 8 is a stereogram showing an ancillary frame is assembled to a main frame according to the present invention.

Referring to FIG. 8, in assembling of the present invention, the lower end of the connecting part (3) is provided with two clip parts (32), and the main frame (1) is provided with two clamping parts (11) at a central bottom thereof for correspondingly clamping and positioning the two clip parts (32). In this way, the connecting part (3) can be positioned on the main frame (1). Then, the inserting sheet (41) of the adjusting element (4) is inserted into one of the plurality of engaging slots (31) for positioning. The position of one of the plurality of engaging slots (31) to be inserted can be selected or adjusted depending on the height of the nose of a wearer. Furthermore, the inserting sheet (41) is provided with a plurality of protrusions (411), and the plurality of engaging slots (31) are provided with a plurality of engaging holes (311) for correspondingly engaging with the plurality of protrusions (411) so that the wearer can adjust the height of the ancillary frame (2) and the distance from the connecting part (3) to the ancillary frame (2) according to the needs.

After the appropriate height and distance are adjusted, the orientation part (42) of the adjusting element (4) is embedded in and engaged with the receiving slot (51) of the engaging part (5) on the ancillary frame (2) so that the angles and positions of the ancillary frame (2) can be adjusted and positioned by the receiving slot (51). Specifically, the orientation part (42) is provided with a plurality of first positioning ribs (421), and the receiving slot (51) is provided with a plurality of second positioning ribs (511) for correspondingly engaging with the plurality of first positioning ribs (421) to rotate and position. Accordingly, the present invention achieves the effect of adjusting the viewing angle.

In addition to being assembled to each other by the structures of the plurality of first positioning ribs (421) and the plurality of positioning ribs (511), the orientation part (42) and the receiving slot (51) may also be assembled to each other by corresponding structures, e.g. a convex portion and a groove.

What is claimed is:

1. An eyeglasses assembling structure having an ancillary frame, comprising:
    a main frame;
    an ancillary frame assembled in the main frame;
    a connecting part assembled to the main frame at a lower end thereof and having a plurality of engaging slots at an upper end thereof;
    an adjusting element having an inserting sheet at a first end thereof and an orientation part at a second end thereof, wherein the inserting sheet is engaged with one of the plurality of engaging slots for positioning; and
    an engaging part disposed on the ancillary frame and having a receiving slot for engaging with the orientation part of the adjusting element to adjust angles and positions.

2. The eyeglasses assembling structure having an ancillary frame as claimed in claim 1, wherein the inserting sheet is provided with a plurality of protrusions, and wherein the plurality of engaging slots are provided with a plurality of engaging holes for correspondingly engaging with the plurality of protrusions.

3. The eyeglasses assembling structure having an ancillary frame as claimed in claim 2, wherein the orientation part is provided with a plurality of first positioning ribs, and wherein the receiving slot is provided with a plurality of second positioning ribs for correspondingly engaging with the plurality of first positioning ribs to rotate and position.

4. The eyeglasses assembling structure having an ancillary frame as claimed in claim 3, wherein the lower end of the connecting part is provided with two clip parts, and wherein the main frame is provided with two clamping parts at a central bottom thereof for correspondingly clamping and positioning the two clip parts.

5. The eyeglasses assembling structure having an ancillary frame as claimed in claim 4, wherein the main frame is a wind goggle, a snow goggle or an industrial goggle.

6. The eyeglasses assembling structure having an ancillary frame as claimed in claim 4, wherein the ancillary frame is optical glasses.

7. The eyeglasses assembling structure having an ancillary frame as claimed in claim 1, wherein the orientation part is provided with a plurality of first positioning ribs, and wherein the receiving slot is provided with a plurality of second positioning ribs for correspondingly engaging with the plurality of first positioning ribs to rotate and position.

8. The eyeglasses assembling structure having an ancillary frame as claimed in claim 7, wherein the lower end of the connecting part is provided with two clip parts, and wherein the main frame is provided with two clamping parts at a central bottom thereof for correspondingly clamping and positioning the two clip parts.

9. The eyeglasses assembling structure having an ancillary frame as claimed in claim 8, wherein the main frame is a wind goggle, a snow goggle or an industrial goggle.

10. The eyeglasses assembling structure having an ancillary frame as claimed in claim 8, wherein the ancillary frame is optical glasses.

\* \* \* \* \*